United States Patent [19]

Comai

[11] Patent Number: 4,762,785
[45] Date of Patent: Aug. 9, 1988

[54] NOVEL METHOD AND COMPOSITIONS FOR INTRODUCTING ALIEN DNA IN VIVO

[75] Inventor: Luca Comai, Davis, Calif.

[73] Assignee: Calgene, Inc., Davis, Calif.

[21] Appl. No.: 796,484

[22] Filed: Nov. 6, 1985

Related U.S. Application Data

[63] Continuation of Ser. No. 407,525, Aug. 12, 1982, abandoned.

[51] Int. Cl.$^4$ .................. C12N 15/00; C12N 1/20; C12P 21/00; C12P 19/34
[52] U.S. Cl. .................. 435/172.3; 435/68; 435/91; 435/172.1; 435/253; 435/320; 935/23; 935/27; 935/29; 935/55; 935/56; 935/64; 935/67; 935/72; 935/73
[58] Field of Search .................. 435/68, 70, 91, 172.3, 435/253, 317, 320, 172.1; 935/23, 27, 29, 55, 56, 64, 67, 72, 73

[56] References Cited

PUBLICATIONS

Hooykaas, "Plasmid Genes Essential for the Interactions of Argobacteria and Rhizobia with Plant cells", in *Molecular Genetics of the Bacteria–Plant Interaction*, Puhler (ed.), Springer–Verlag, Berlin, 1983, pp. 229–239.
Thomashow et al., "Integration and Organization of Ti Plasmid Sequences in Crown Gall Tumors", Cell, 19: 729, (1980).
Petit et al.: Nature, 271, 570, (1978).
Low et al.: Ann. Rev. Genet., 12, 249, (1978).
Eisenstark: Ann. Rev. Genet., 11, 369, (1977).
Matzke et al.: Chem. Abstr. 95:111256u, (1981), of J. Mol. Appl. Genet., 1, 39, (1981).
Ditta et al., Proc. Natl. Acad. Sci. USA, (1980), 77:7347–7351.
Ruvkun and Ausubel, Nature, (1981), 289:85–88.

Primary Examiner—James Martinell
Attorney, Agent, or Firm—Bertram I. Rowland

[57] ABSTRACT

Method and compositions are provided for introducing alien DNA into a nucleic acid in vivo by providing a plasmid capable of replication in a first host, which is capable of conjugation with a second host into which the alien DNA is to be introducted. The plasmid is characterized by being capable of maintenance in said first host, being incapable of maintenance in said second host, having a region of homology with DNA present in said second host, not self-transmissable but capable of mobilization by a helper plasmid and having a marker, which may be the alien DNA, for selection in said second host. The invention finds particular application for introducing alien DNA into the Ti plasmid of *Agrobacterium tumefaciens* for introduction into plant cells.

7 Claims, No Drawings

NOVEL METHOD AND COMPOSITIONS FOR INTRODUCING ALIEN DNA IN VIVO

CROSS REFERENCE TO RELATED APPLICATIONS

This application is a continuation of U.S. application Ser. No. 407,525, filed Aug. 12, 1982, now abandoned, which disclosure is incorporated herein by reference.

BACKGROUND OF THE INVENTION

1. Field of the Invention

There are many situations where it is desirable to introduce alien DNA into a particular segment of a chromosome or extrachromosomal element. Frequently, this can be very cumbersome because of the numerous steps involved in cloning the alien DNA, isolating the alien DNA, finding appropriate restriction sites and introducing the alien DNA into the host of interest. There are many aspects to be considered in a useful method. Small plasmids are desirable, since they are easy to work with, readily manipulated, and generally have few restriction sites for a particular restriction enzyme, frequently providing a number of unique restriction sites. Thus, they are readily manipulatable.

Other considerations are efficiency of transformation or conjugation, stability or maintenance of the alien DNA in the host, the genetic environment and control of the alien DNA, and the like. Further considerations include the ease with which the presence of the alien DNA can be determined, purification of the alien DNA, by itself and in conjunction with DNA segments to which it is attached, and the ease of introduction and excision of the alien DNA into and out of a vector.

Exemplary of the problems described above is the modification of large naturally occurring plasmids, such as the Ti plasmid of A. tumefaciens. The large size of the plasmid makes manipulation difficult, impedes isolation and purification, as well as identification of the introduction of alien DNA and the opportunity for excision.

2. Description of the Prior Art

Ditta et al. PNAS USA (1980) 77:7347-7351 describe a broad host range DNA cloning system for Gram-negative bacteria. Ruvkun and Ausubel, Nature (1981) 289:85-88 describe a general method for site directed mutagenesis in prokaryotes. Thomashow et al. Cell (1980) 19:729-739 describe the integration and organization of Ti plasmid sequences in crown gall tumors, as well as the construction of the plasmid pNW33C-19-1.

SUMMARY OF THE INVENTION

A unicellular microorganism is transformed with an extrachromosomal element capable of maintenance in such first host, where the extrachromosomal element is characterized by being self-transmissable or capable of mobilization with a second helper extrachromosomal element; being capable of conjugal transfer to a host of interest (second host); having a narrow host range replication system; containing predetermined DNA segments comprising alien DNA and DNA homologous with a DNA sequence in said second host, either chromosomal or extrachromosomal and a marker allowing for selection.

DESCRIPTION OF THE SPECIFIC EMBODIMENTS

In accordance with the subject invention, methods and compositions are provided for introduction of alien DNA in vivo by conjugation between a first host and a second host. The introduction is achieved with an extrachromosomal element characterized by having a replicon having a narrow host range, being self-transmissable or capable of mobilization with a helper plasmid, being incapable of maintenance in the exconjugant or target host, having a region of homology with target DNA in the second host, having alien DNA capable of replication, transcription and usually translation in a host cell, and having one or more markers selectable in the target host.

The two hosts are unicellular microorganisms, particularly prokaryotes. Of particular interest is the use of E. coli as the first host and A. tumefaciens as the exconjugant or transconjugant second host.

The extrachromosomal elements which are the compositions of this invention have a vector having a replicon or replication system having a narrow host range. That is, they are capable of maintenance and replication in a first unicellular host which is capable of conjugation with a second host of interest having the target DNA, but the vector is incapable of maintenance in the target or second host, so that the target host is rapidly cured. In this way, in the absence of integration of at least a portion of the extrachromosomal composition, the extra chromosomal DNA will be lost in the second host. Thus, the DNA of the extrachromosomal element is rescued by integration with a stable genetic element of the target host.

The replicon may come from a plasmid, virus, or other source which allows for stable maintenance in the first host. The first host will normally be a prokaryote, particularly E. coli. By employing a vector capable of replication in E. coli and other enteric hosts (narrow range), the vector will not be replicated and maintained in non-enteric Gram negative bacteria. The extrachromosomal element may therefore be a plasmid or virus (phage) or other DNA, which provides the requisite properties.

The extrachromosomal element will also have a mobilization locus, and will be self-transmissable, or capable of transfer to another host with a helper plasmid having the necessary genes for transfer, e.g. tra.

Another characteristic is the presence of a DNA sequence homologous with DNA present in the target host to provide for efficient integration. The homologous DNA in the target or second host which serves as the recombination locus may be chromosomal or extra chromosomal. Of particular interest for target DNA is the Ti plasmid in A. tumefaciens, which may be wild strain, a mutant, or containing alien DNA as a result of rDNA or other technique for introduction of alien DNA, e.g. transposon. More particularly of interest, is the T-region of the Ti plasmid of A. tumefaciens.

The region of homology will generally be at least about 600 bp, usually 1000 bp or more, usually not exceeding about 5000 bp, and more usually not exceeding about 3000 bp. The region of homology may include regions encoding proteins, regulatory regions, or non-encoding regions and need not have perfect homology.

One or more segments of alien DNA will be included in the plasmid, normally encoding one or more proteins of interest. The DNA will be alien to the prokaryote involved in the mating. The protein of interest may be any protein derived from any convenient source, either prokaryotic or eukaryotic, including lower or higher orders of eukaryotes, e.g. fungi, algae, protozoa, mammals, plants, etc. The protein expressed may provide a new function for the host organism or a product which is desired separate from the host organism, e.g. a mammalian protein such as a mammalian hormone.

There can be two types of integration: a single crossover or a double crossover. In the single crossover, the entire extrachromosomal element becomes integrated into the DNA of the target host. With a double crossover, a portion of the extrachromosomal element is substituted for a portion of the target host DNA.

By having regions of homology with the target DNA on both sides of the alien DNA and in close proximity to the termini of the alien DNA, the alien DNA may be inserted into the target host DNA without including much of the remaining DNA of the extrachromosomal element.

With the Ti plasmid, there is the further interest of introducing the alien DNA into a plant susceptible to tumor induction by the Ti plasmid. Thus, the subject method provides the opportunity to introduce alien DNA into a plant, where the alien DNA may be expressed under the control of the regulatory signals present in the Ti plasmid. The subject method therefore provides a simple technique for modifying the genome of the plant cell through the use of a modified Ti plasmid as the modifying agent.

The alien DNA may be solely a gene encoding a protein of interest or may be present with other genes, regulatory signals, or the like. For example, a promoter may be provided which is native to the Ti plasmid or the ultimate plant cell, where the alien gene would not be capable of expression in the prokaryote but only in the eukaryotic plant cell. The promoter may provide for regulation in the plant cell or constitutive production. Various genes may be combined with the gene of interest to provide for amplification of the gene of interest, where the other genes respond to stress by resulting in tandem reiteration of such other gene in conjunction with flanking DNA regions, e.g., genes expressing DHFR, metallothioneins, etc.

While not always essential, particularly where the alien DNA provides a means for selection, it will usually be desirable to provide a marker as part of the extrachromosomal composition of this invention. The marker will allow for selection of exconjugants. A wide and diverse variety of markers may be employed.

Conveniently, antibiotic resistance may be employed, which allows for selection of exconjugants by culturing the cells on a medium containing the particular antibiotic. Antibiotic resistance can be provided to ampicillin, penicillin, tetracycline, kanamycin, etc. Resistance can also be provided to heavy metals by employing genes that express metallothioneins. These genes may also be employed as amplifying genes. Genes may be provided for selecting against toxins, such as colicin. Other genes provide immunity to viruses.

Alternatively, prototrophy can be provided to an auxotrophic host. By culturing the exconjugants in a culture medium lacking the essential metabolite, the exconjugants will be selected for by being capable of multiplication. In many instances, it will be desirable to have a plurality of markers, particularly if one of the markers has a restriction site for insertion of the alien DNA. The loss of the property provided by the marker allows for detection of the extrachromosomal DNA into which the alien DNA has been inserted by double selection.

The extrachromosomal DNA into which the alien DNA is introduced will desirably have at least one and preferably a plurality of unique restriction sites. A wide variety and increasing number of restriction enzymes are commercially available, so that one has the opportunity to sequence the extrachromosomal DNA and/or prepare a restriction map to develop a synthetic scheme for the final composition. A wide variety of restriction enzymes are known, such as EcoRI, PstI, HindI, II, and III, HaeII, KpnI, HpaI, XhoI, and SmaI, as illustrative but not exhaustive of restriction enzymes.

As already indicated, the subject composition must be self-transmissible or capable of conjugal transfer by trans-complementation with a helper plasmid. Conveniently, the extrachromosomal DNA and the helper plasmid will be initially employed in different cells, employing tripartite rather than dual mating, rather than requiring the in vitro introduction of both the extrachromosomal DNA and the helper plasmid into the first host cell prior to conjugal transfer. The helper plasmid will have the necessary function for conjugal mobilizability (transfer), as well as a functioning replication system.

The subject extrachromosomal DNA will normally be prepared from a vector derived from a plasmid or virus, more usually a plasmid, by modification of the plasmid to provide the desired properties, and inserting the appropriate DNA sequences in the appropriate order in available restriction sites. However, various techniques can be used, such as primer repair or in vitro mutagenesis for introduction of DNA into the vector. The manner of preparing the extrachromosomal composition is conventional in that the technique will normally involve restriction at specific sites to provide for blunt or cohesive ends, direct introduction of the DNA of interest, or through the use of linkers, tailing, or the like, ligation, cloning, followed by repeating the process for introduction of additional DNA sequences. Thus, after each addition of new DNA into the vector, the vector will be recircularized and cloned, followed by selecting for the vector having the newly introduced DNA sequence.

Once the extrachromosomal DNA has been completed, it will be introduced into the first host. Transfer can then be achieved by combining the first host, the second target or recipient host, and the host having the helper or mobilizing plasmid under conditions to provide for mating of the three strains. One then selects for the ex- or transconjugant by the markers introduced into the vector. In the case of *A. tumefaciens*, the Ti plasmid may be restricted with appropriate restriction enzymes and compared with the wild strain or target Ti plasmid to demonstrate the introduction of the alien DNA.

The following examples are offered by way of illustration and not by way of limitation.

EXPERIMENTAL

Methods and Materials

A 4.6 Kb fragment from the Ti plasmid pTiA6 generated by digestion with endonuclease BamH1 is referred to as "Bam19". Plasmid pNW33C-19-1 is constructed by the insertion of Bam19 in pBR325 (Thomashow et al., 1980, supra; Bolivar, Gene (1978) 4:121–126). Plasmid pCGN402 is a derivative of pNW33C-19-1 in which a kanamycin resistance determinant is inserted in the unique SmaI site of Bam19. pNW33C-19-1 is digested with SmaI and BglII linkers inserted to give pCGN401, which has a BglII site replacing the SmaI site. The kanamycin resistance gene obtained from pUC5 by BamHI digestion is then inserted into the BglII site. The particular KAN$^r$ gene is chosen because of convenient SalI restriction sites at its termini, allowing for subsequent excision. Four different transformants of E. coli are prepared by introduction in accordance with conventional techniques of four different plasmids: (1) pBR325; (2) pNW33C-19-1; (3) pCGN402; and (4) pRK2013.

The strains employed have the following characteristics: E. coli K12 HB101 (F$^-$, pro, leu, thi, loc Y str$^r$, hsdR, hsdM, endoI, recA, ara14, galK$_2$, xy15, mtl1, supE44). (Boyer and Roulland, J. Mol. Bio. (1969) 41:459–472). E. coli K12 mm294 (F$^-$, pro, thi, endoI, hsdR). (Gilbert et al. Gene (1980) 12:235-241). A. tumefaciens A348 (pTiA6) rif$^r$, cm$^r$, nal$^r$. (Watson et al., J. Bacteriol. (1975) 123:255-264; Chilton, et al, Genetics (1976) 83:609–618)

Matings were performed as follows. Each of the strains was cultured in 10 ml of YT (trystone medium) overnight, except for the A. tumefaciens which was cultured in LB/AE. The matings were performed by combining 4ml of A. tumefaciens A348, 2ml of E. coli HB101 (pRK2013) and 2ml of the donor strain. The cell suspensions were mixed in a Falcon tube and then filtered onto a 0.45µ millipore filter. The filters were incubated overnight on LB/AE at 30° C., followed by removal of the filter from the medium and washing in 0.5 ml water.

The cells were then diluted to various dilutions and plated on selective media.

The matings were carried out as described above and the following table indicates the strains employed, the selective media, and the observations at various cell dilutions.

mixture containing 2 µl of DNA, 2 µl of enzyme, 2 µl of buffer, and 14µl of water to provide a final volume of 20 µl and the digest carried out at 37° for 100 min. The digestion was stopped by the addition of 10 µl of tracking dye and the entire sample loaded on 0.7% agarose and the electrophoresis carried out at 100 v for 180 min.

The results of the various digests are as follows. The BamH1 pattern from pTiA6-E1 showed two new bands of about 6 kb each, which were pBR325 and a 4.6 kb Bam19 fragment containing a 1.4 kb Kan$^r$ insert. The EcoRI pattern gave a new 9.5 kb fragment which was part Eco7 with a kanr insert. With HindIII, a new 8.6 kb band was present while a 12.6 kb band was missing. The missing one was HindI, while the new one was part of HindI plus a portion of Kan$^r$.

Other new fragments appeared to be present but could not be readily characterized since they comigrated with other fragments generated from pTiA6-E1. However, the observed differences clearly differentiate pTiA6-E1 from the wild type plasmid pTiA6 and demonstrates that pCGN402 has integrated into pTiA6.

In accordance with the subject invention, a simple, efficient method is provided for introducing DNA into a host, particularly into an extrachromosomal element of a host. By employing a readily available safe host as the donor strain, for which a large number of well characterized plasmid or viral vectors are available, foreign DNA can be readily transferred to a wide variety of prokaryotic hosts and alien DNA introduced into the DNA of such prokaryotic hosts in a stable manner. Furthermore, by employing a recipient strain, such as A. tumefaciens, which is capable of transferring DNA to a higher cell order, namely plant cells, one can transfer alien DNA from a simple prokaryote, such as E. coli, to the higher order plant cells through the intermediacy of the Ti plasmid. High efficiencies of integration can be achieved through the stable integration of large DNA segments of alien DNA.

Although the foregoing invention has been described in some detail by way of illustration and example for

TABLE I

| Mating Strains[1] | | | Selection[2] | | | Observation[3,4] | | |
|---|---|---|---|---|---|---|---|---|
| | | Re- | Rif | Kan | Carb | Dilution Cells | | |
| Donor | Mab. | cipient | 5 µg/ml | 50 µg/ml | 50 µg/ml | $10^{-3}$ | $10^{-4}$ | $10^{-5}$ |
| 402 | 2013 | 348a | X | X | | bgd + ~200 larger white colonies | bgd + ~49 larger white colonies | bgd + 2 larger white colonies |
| C19 | ds | ds | X | | X | bgd of ~1000 colonies + 50 larger white colonies | bgd + 5 larger white colonies | bgd |
| 325 | ds | ds | X | | X | confluent lawn | ~2000 colonies | bgd of very small white colonies + ~300 larger white colonies |

[1]Donor 402—E. coli mm294 (pCGN402) C19—E. coli HB101 (pNW33C-19-1) 325—E. coli HB101 (pBR325) Mab. 2013 E. coli HB101 (pRK2013) Recipient 348a—A. Tumefaciens A348a
[2]Rif—rifampicin Kan—kanamycin Carb—carbenillin
[3]bgd—background
[4]Selection for ampicillin resistance in A. tumefaciens strain 348a leads to the isolation of spontaneous resistance mutants. For this reason, the experiments using C19 and 325 as donors are inconclusive.

The selection of exconjugants was complicated by the appearance of spontaneous resistant colonies of Agrobacterium. These could, however, be distinguished from true exconjugants as they appeared, on average, a day later.

A restriction digest of Ti plasmid resulting from the mating with the donor 402 was compared with a restriction digest of the wild type Ti plasmid, employing EcoRI, BamH1, XhoI and HindIII using a restriction purposes of clarity of understanding, it will be obvious that certain changes and modifications may be practiced within the scope of the appended claims.

The strain E. coli K12 mm294 (pCGN402) was deposited for patent purposes at the American Type Culture Collection, Rockville, MD, USA on Aug. 5, 1982 and given accession no. 39171.

What is claimed is:

1. A method for stably inserting alien DNA into the DNA of the Ti plasmid of *A. tumefaciens*, said method comprising:
   mating with said *A. tumefaciens* a first *E. coli* host containing, a first extrachromosomal element characterized as having: a narrow range replication system incapable of maintenance in said *A. tumefaciens*; a DNA sequence homologous with a DNA sequence of the T region of the Ti plasmid present in said *A. tumefaciens*; mobilization capability being self-transmissible or capable of transfer with a helper plasmid; a segment comprising alien DNA; and a marker capable of selection in said *A. tumefaciens* with the proviso that if the first extrachromosomal element is not self-transmissible, the first *E. coli* host also contains a second extrachromosomal element as said helper plasmid having a narrow range replication system and incapable of replication in said *A. tumefacians*: and genes capable of imparting transmissibility to said first and second extrachromosomal elements; and
   selecting by means of said marker an exconjugant.

2. A method according to claim 1, wherein said second extrachromosomal element is introduced into said *E. coli* host by mating with a host capable of conjugation with said *E. coli* host.

3. A method according to claim 1, including the additional step of infecting a plant cell with said exconjugant.

4. A method for stably inserting alien DNA into the T region of the Ti plasmid, said method comprising:
   mating an *A. tumefaciens* host containing a Ti plasmid with an *E. coli* host containing first and second extrachromosomal elements,
   said first element:
   having a replication system recognized by said *E. coli*, but not by *A. tumefaciens*;
   having a region of homology of at least 800 bp with said T region;
   having alien DNA;
   containing a mobilization locus, either being self-transmissible or using a second element as a helper plasmid; and
   having a marker capable of selection in said *A. tumefaciens*;
   said second element:
   having a replication system recognized by *E. coli*, but not *A. tumefaciens*; and
   having genes capable of imparting transmissibility to said first element, and
   selecting for an *A. tumefaciens* exconjugant containing said alien DNA by means of said marker.

5. A method according to claim 4, wherein said alien DNA is inserted into said region of homology.

6. A method according to claim 4, wherein said second extrachromosomal element is introduced into said *E. coli* by mating.

7. A method according to any one of claims 4, 5, or 6, including the additional step of infecting a plant cell with said exconjugant.

* * * * *